(12) United States Patent  
Charlton et al.

(10) Patent No.: US 8,940,540 B2
(45) Date of Patent: Jan. 27, 2015

(54) SENSOR STORAGE AND DELIVERY SYSTEM WHERE THE TEST SENSORS ARE INDIVIDUALLY FOILED AND ARRANGED IN A STACK

(71) Applicant: Bayer Healthcare LLC, Tarrytown, NY (US)

(72) Inventors: Steven C. Charlton, Osceola, IN (US); Allen Brenneman, Goshen, IN (US)

(73) Assignee: Bayer HealthCare LLC, Whippany, NJ (US)

( * ) Notice: Subject to any disclaimer, the term of this patent is extended or adjusted under 35 U.S.C. 154(b) by 32 days.

(21) Appl. No.: 13/796,093

(22) Filed: Mar. 12, 2013

(65) Prior Publication Data

US 2013/0323852 A1  Dec. 5, 2013

Related U.S. Application Data

(60) Provisional application No. 61/653,801, filed on May 31, 2012.

(51) Int. Cl.
G01N 33/66 (2006.01)
G01N 35/00 (2006.01)
B01L 3/00 (2006.01)
G01N 33/543 (2006.01)

(52) U.S. Cl.
CPC .......... *G01N 33/66* (2013.01); *G01N 33/54386* (2013.01); *G01N 2333/904* (2013.01)
USPC .................. 436/46; 436/48; 436/95; 422/408; 422/413; 422/554; 422/563; 422/570; 435/14

(58) Field of Classification Search
USPC .................. 436/43, 46, 48, 63, 95, 149, 150; 422/408, 413, 68.1, 82.01, 82.02, 554, 422/560, 561, 563, 568–570; 435/14
See application file for complete search history.

(56) References Cited

U.S. PATENT DOCUMENTS

| | | | | |
|---|---|---|---|---|
| 5,854,074 A | * | 12/1998 | Charlton et al. | 436/46 |
| 6,881,578 B2 | * | 4/2005 | Otake | 436/44 |
| 7,270,247 B2 | * | 9/2007 | Charlton | 221/59 |
| 7,723,113 B2 | * | 5/2010 | Charlton | 436/46 |
| 7,875,243 B2 | * | 1/2011 | Rush et al. | 422/68.1 |
| 8,691,161 B2 | * | 4/2014 | Fleming | 422/412 |
| 2008/0131322 A1 | * | 6/2008 | Kheiri et al. | 422/82.01 |
| 2013/0324822 A1 | * | 12/2013 | Prais et al. | 600/365 |

* cited by examiner

*Primary Examiner* — Maureen Wallenhorst (74) *Attorney, Agent, or Firm* — Lerner, David, Littenberg, Krumholz & Mentlik, LLP (57) ABSTRACT

A portable, hand-held glucose testing device includes a housing configured to accommodate a plurality of test sensors in a stacked arrangement and having a wall with an opening defined therein. A plurality of packaged test sensors is stacked in alignment with one another within the housing. Each of the test sensors is packaged within a blister package. The blister package includes a blister package housing and a cover foil overlying a surface of the blister package housing and the test sensor. A drive slide is configured to displace one of the plurality of packaged test sensors out of alignment with other packaged test sensors. A knife mechanism is configured to pierce through the cover foil, and to engage and urge the test sensor to extend through the opening for receiving a sample. A meter contact is configured to engage the test sensor when the test sensor extends through the opening.

19 Claims, 7 Drawing Sheets

SENSOR STORAGE AND DELIVERY SYSTEM WHERE THE TEST SENSORS ARE INDIVIDUALLY FOILED AND ARRANGED IN A STACK

CROSS REFERENCE TO RELATED APPLICATIONS

This application claims the benefit of the filing date of the U.S. Provisional Patent Application No. 61/653,801, filed on May 31, 2012, the disclosure of which application is hereby incorporated by reference herein in its entirety.

FIELD OF INVENTION

The present invention relates to fluid monitoring devices and the distribution of test sensors stored within the fluid monitoring devices.

BACKGROUND OF THE INVENTION

It is often necessary to quickly obtain a sample of blood and perform an analysis of the blood sample. One example of a need for obtaining a sample of blood is in connection with a blood glucose monitoring system, which a user must frequently use to monitor the user's blood glucose level.

Those who have irregular blood glucose concentration levels are medically required to regularly self-monitor their blood glucose concentration level. An irregular blood glucose level can be brought on by a variety of reasons including illness such as diabetes. The purpose of monitoring the blood glucose concentration level is to determine the blood glucose concentration level and then to take corrective action, based upon whether the level is too high or too low, to bring the level back within a normal range. The failure to take corrective action can have serious implications. When blood glucose levels drop too low—a condition known as hypoglycemia—a person can become nervous, shaky and confused. That person's judgment may become impaired and that person may eventually pass out. A person can also become very ill if their blood glucose level becomes too high—a condition known as hyperglycemia. Both conditions, hypoglycemia and hyperglycemia, are potentially life-threatening emergencies.

One method of monitoring a person's blood glucose level is with a portable, hand-held blood glucose testing device. The portable nature of these devices enables the users to conveniently test their blood glucose levels wherever the user may be. The glucose testing device includes a test strip to harvest the blood for analysis. One type of test strip is the electrochemical test strip. The electrochemical test strip includes a regent designed to react with glucose in the blood to create an oxidation current at electrodes disposed within the electrochemical test strip which is directly proportional to the users blood glucose concentration. Such a test strip is described in U.S. Pat. Nos. 5,120,420, 5,660,791, 5,759,364 and 5,798,031, each of which is incorporated herein in its entirety. Another type of sensor is an optical test strip, which incorporates a reagent designed to produce a colorimetric or fluorescent reaction indicative of a user's blood glucose concentration level. The colorimetric reaction is then read by a spectrometer incorporated into the testing device. Such optical test strips are described in U.S. Pat. Nos. 5,194,393 and 7,477,404, each of which is incorporated herein by reference in its entirety.

In order to check a person's blood glucose level, a drop of blood is obtained from the person's fingertip using a lancing device, and the blood is harvested using the test strip. The test strip, which is inserted into a testing unit, is brought into contact with the blood drop. The test strip draws the blood, via capillary action, inside the test strip and the ensuing electrochemical reaction is measured by the test unit which then determines the concentration of glucose in the blood. Once the results of the test are displayed on a display of the test unit, the test strip is discarded. Each new test requires a new test strip.

Figure 1:
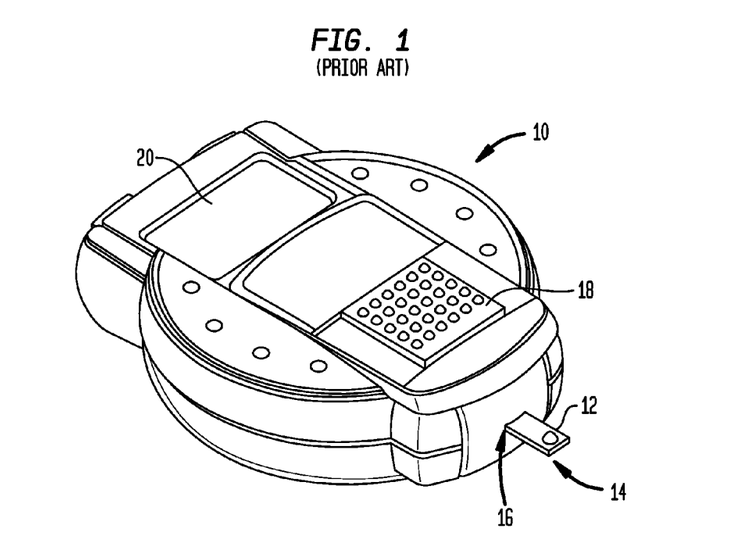
FIG. 1 is a perspective view of a prior art test meter.
Figure 2:
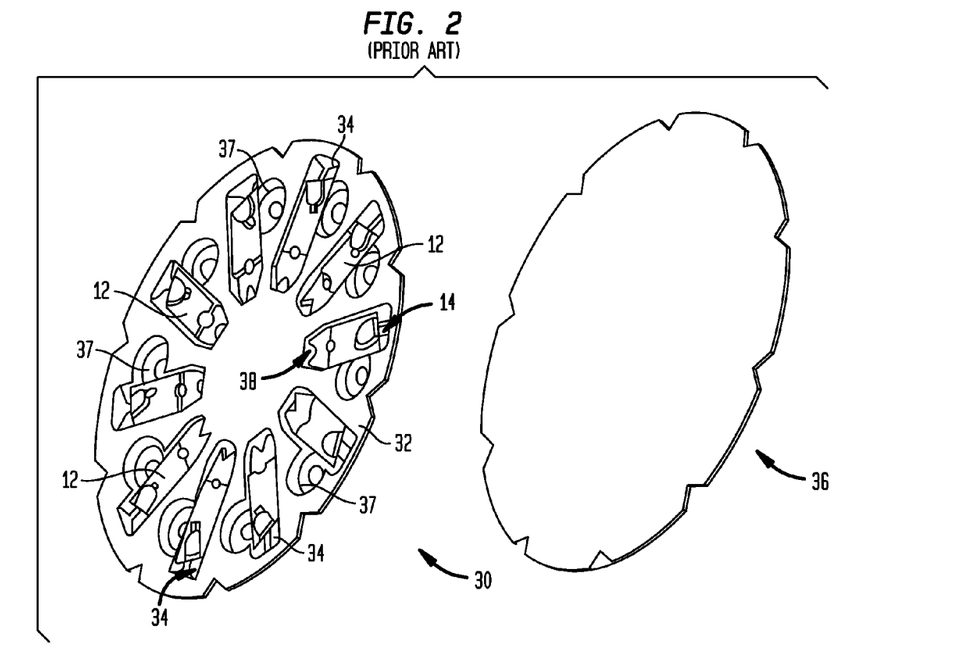
FIG. 2 is a perspective view of a prior art cartridge that can be used in the meter shown in FIG. 1.

Referring now to FIGS. 1 and 2, an example of a testing device 10 and a package 30 of test strips 12 ("test strip pack") are shown, respectively. The test strip pack 30 is designed to be housed within the testing device 10. Prior to each test, a collection area 14 of an individual test strip 12 is pushed by a mechanism within the testing device 10 through its packaging and is extended from the testing device 10 through a slot 16 for harvesting a sample of blood. The testing device 10 includes a slider 18 for advancing the test tensor 12. In FIG. 1, a test strip 12 is shown extending from the testing device 10. The collection area 14 extends from the testing device 10, while a contact area, disposed at the opposite end of the test strip 12 shown in FIGS. 1 and 2, remains inside the testing device 10. The contact area includes terminals that electrically couple the electrodes to a meter disposed within the testing device 10 for measuring the oxidation current produced at the electrodes by the reaction of glucose and the reagent. The test unit includes a display 20.

Referring now to FIG. 2, test strips 12 are shown disposed in the test strip pack 30. The test strip pack 30 is made up of a circular disk 32 having only ten individual compartments (blisters) 34 arranged radially. The disk is made from an aluminum foil/plastic laminate which is sealed to isolate the sensor from ambient humidity and from other sensors with a burst foil cover 36. Each test strip 12 is kept dry by a desiccant located inside a desiccant compartment 37 disposed adjacent to the compartment 34.

To retrieve a test strip, a mechanism disposed within the testing device 10, such as a knife, is driven down through the burst foil into an individual elongated compartment 34 at the end closest to the hub of the disk 32 and then moved radially toward the perimeter of the blister 34. In doing so, the knife engages the contact area 38 (fish tail) of the sensor in that compartment. Radial travel of the knife pushes the tip of the sensor out through the burst foil 36 and through parts of the testing device 10 such that the collection area 14 of the sensor 12 is completely out of the testing device 10 and ready to receive a fluid test sample such as blood. For this stage, it is essential that the bond between the base and lid of the test strip withstand the sheer forces generated when the test strip bursts out through the foil 36. This method of providing a test strip ready for use is more fully described in U.S. Pat. No. 5,575,403, which is incorporated herein by reference in its entirety.

Further details of the operational and mechanical aspects of the testing device 10 and test strip pack 30 are more fully described in U.S. Pat. Nos. 5,575,403, 5,630,986, 5,738,244, 5,810,199, 5,854,074 and 5,856,195, each of which are hereby incorporated by reference in their entireties.

A drawback associated with this flat array of testing devices is the large area that is occupied. The size of testing devices that internally house such a flat array package constrains the size of the package (i.e., the number of test strips), thus making it difficult to increase the number of test strips per package. Accordingly, there exists a need for a testing system capable of storing and dispensing numerous test strips.

BRIEF SUMMARY OF THE INVENTION

An embodiment of the invention includes an analyte testing device comprising a housing configured to accommodate a plurality of test sensors in a stacked arrangement and having a wall with an opening defined therein. The testing device may be hand-held. A plurality of packaged test sensors is stacked in alignment with one another within the housing. Each of the test sensors is packaged within a blister package. The blister package comprises a blister package housing and a cover foil overlying a surface of the blister package housing and the test sensor. A drive slide is configured to displace one of the plurality of packaged test sensors out of alignment with other packaged test sensors. A knife mechanism is configured to pierce through the cover foil, and to engage and urge the test sensor to extend through the opening for receiving a sample. A meter contact is configured to engage the test sensor when the test sensor extends through the opening.

According to an aspect of the invention, a method for testing blood glucose comprises accommodating a plurality of individually packaged test sensors in a test meter and causing a first mechanism in the test meter to extract a test sensor out of a package. The method further comprises positioning the test sensor to extend out of the meter for receiving a sample and causing a second mechanism in the test meter to urge the package to extend out of the meter.

According to another embodiment of the invention, a portable, hand-held glucose testing device comprises a housing configured to accommodate a plurality of test sensors in a stacked arrangement and having a wall with an opening defined therein. A plurality of test sensors is disposed in a stacked arrangement, wherein each of the test sensors is individually packaged in a blister package and a cover foil. A drive slide is configured to selectively remove one of the plurality of test sensor packages out of the stacked arrangement. A knife mechanism is configured to pierce through the cover foil, and to engage and urge the test sensor to extend out of the opening for receiving a sample. A meter contact is configured to engage the test sensor when the test sensor extends through the opening if the planned measurement is by electrochemistry. If an optical or fluorimetric measurement is contemplated then the test sensor could be engaged by a pin if desired.

BRIEF DESCRIPTION OF THE DRAWINGS

Various embodiments of the present invention will now be discussed with reference to the appended drawings. It is to be appreciated that these drawings depict only some embodiments of the invention and are therefore not to be considered limiting of its scope.

DETAILED DESCRIPTION

The following discussion describes, in detail, various aspects and embodiments of the present invention. This discussion should not be construed as limiting the invention to those particular aspects or embodiments. Rather, practitioners skilled in the art will recognize numerous other aspects and embodiments as well, which are within the scope of the present invention.

In describing the embodiments of the present invention illustrated in the drawings, specific terminology will be used for the sake of clarity. For purposes of explanation, the invention is generally described herein with regard to glucose test meters and test sensors or strips. However, the present invention is not intended to be limited to the specific terms so selected, and it is to be understood that each specific term includes all technical equivalents that operate in a similar manner to accomplish a similar purpose. The presently disclosed meter may contain packaged test sensors designed to determine the concentration of other analytes in other types of samples. For example, test sensors may alternatively measure lipid profiles (e.g., cholesterol, triglycerides, low-density lipoprotein (LDL) and high-density lipoprotein (HDL)), microalbumin, hemoglobin A1c, fructose, lactate, bilirubin, or other analytes. The analytes may be found in, for example, a whole blood sample, a blood serum sample, a blood plasma sample, or other body fluids, such as interstitial fluid (ISF), saliva, and urine. The dimensions provided herein are by way of non-limiting examples only and not intended to limit the scope of the appended claims.

Figure 3:
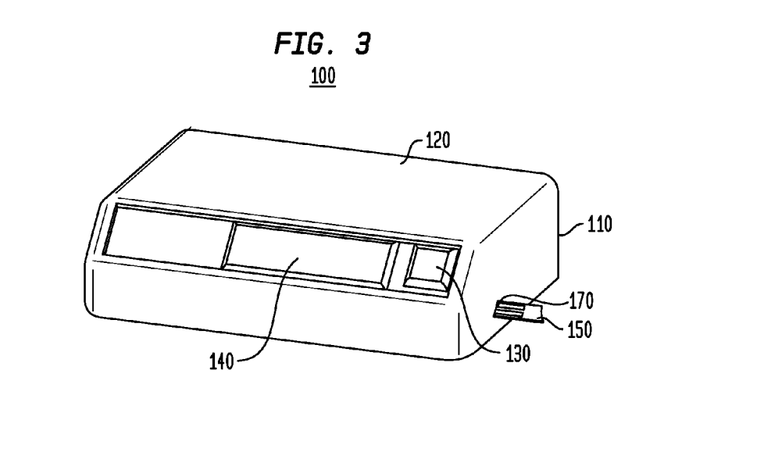
FIG. 3 is a perspective view of a test meter, according to an embodiment of the invention.
Figure 4:
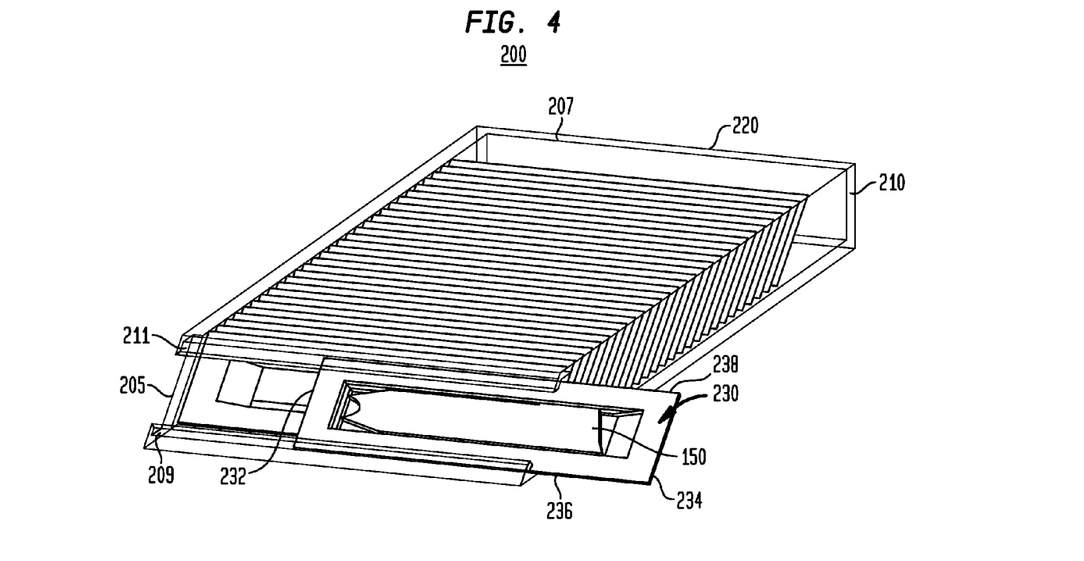
FIG. 4 is a schematic view of a cartridge for use with the meter of FIG. 3, holding a plurality of test sensors, according to an embodiment of the invention.

Referring now to FIG. 3, a test meter 100 is illustrated, according to one embodiment. Meter 100 includes a housing 110 configured to receive a plurality of individually packaged test sensors or strips 230 (FIG. 4) therein. The test sensors 230 (FIG. 4) may be housed in a cartridge 210 (of FIG. 4) to allow for refilling of the test meter 100 with new packaged test sensors or strips 230 (FIG. 4). Housing 110 includes a top wall 120 which comprises a display, for example, an LCD display, that displays the results of the test. It will be understood, that other types of display technologies may also be used without departing from the scope of the present invention. Meter 100 further includes a sensor release button 130 and a slide driver 140, structures and functions of which shall be described in further detail below. When it is desired to test a fluid sample, a test sensor 150 is placed into a test position. As shown, the test sensor 150 can protrude from housing 110 out of an opening or slot 170 to receive the fluid sample, such as a blood sample. After the test is complete, the sensor release button 130 may be activated to release and discard the used test sensor 150. In an exemplary embodiment, test meter 100 may have dimensions of 75 millimeters (mm)×50 mm×20 mm. It will be understood that based on the requirements of given application, the dimensions of test meter 100 may be varied without departing from the scope of the invention. The test meters disclosed herein are preferably dimensioned so that the meter is compact, portable, and convenient for a user to handle.

Referring now to FIG. 4, a cartridge 200 is illustrated schematically. Cartridge 200 includes an open end 205 and a closed end 207 and. A plurality of packaged test sensors 230 is stacked generally vertically within cartridge 200. The test sensors 230 in the stack may be aligned such that opposed edges 232, 234 of the packaged test sensor 230 in the stack are aligned with one another. In certain embodiments, each of the edges of the test sensor 100 may be aligned. As is evident from FIG. 4, packaged test sensors 230 are stacked at an angle relative to a vertical wall 220 of cartridge 200 so that major surfaces 236, 238 of the test sensor 230 are stacked vertically, one on top of the other. Providing the test sensors 230 at an angle permits the height of the cartridge to be less than the height of the stack of packaged sensors 230 contained therein. In an exemplary embodiment, the tilt angle of packaged sensors 230 may range from between about 0 degrees to 60 degrees. In one embodiment, the packaged sensor 230 may have a tilt angle of about 45 degrees. Each packaged test sensor 230 comprises an individually packaged test sensor 150 and shall be described in further detail below. Cartridge 200 is capable of both, storing a plurality of stacked packaged test sensors 230, and then dispensing each of the plurality of packaged test sensors 230 stored within the cartridge 200 one at a time. In an exemplary embodiment, the slot 170 (FIG. 3) is angled so as to align with the tilt angle of the packaged test sensor 230 in the stack. Thus, the angle of the slot 170 relative to the vertical is generally the same as the tilt angle of the packaged sensor 230 to facilitate deployment of the test sensor 150 from the package 620 through the slot 170.

In the illustrated embodiment, packaged test sensor 230 includes a test sensor 150. For ease of illustration, the foil covering test sensor 150 is not shown in FIG. 4. In this embodiment, packaged test sensors 230 may be biased within cartridge 200 to push the foremost packaged test sensor 230 toward the open end 205 of cartridge 210. In the illustrated embodiment, ridges 209, 211 at the open end 205 of the cartridge 200 retain the foremost packaged test sensor 230 in the cartridge. In another embodiment, a slot (not shown) may be provided in one or more walls of cartridge 210, through which an external biasing mechanism (not shown), for example, disposed in test meter 100 may push the foremost packaged sensor 230 out of cartridge 210. In one embodiment, cartridge 200 may have dimensions of 49 mm×21 mm×15 mm. These dimensions of cartridge 210 can help to ensure that cartridge 210 is accommodated within test meter 100. In one embodiment, cartridge 200 may be configured to hold twenty-five (25) packaged strips or sensors 230. Of course, in other embodiments, cartridge 200 may have different dimensions and may be configured to hold more than or less than twenty-five (25) packaged strips or sensors 230 at a different tilt angle, depending on the requirements of a given application. It will further be understood that the dimensions of test meter 100 may be varied to accommodate a cartridge of given dimensions and vice versa.

Figure 5A:
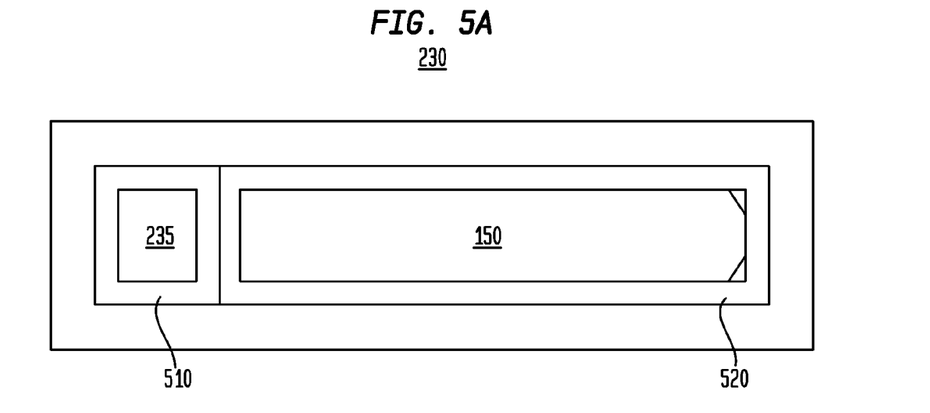
FIGS. 5A and 5B are the top view and the front view of a packaged test sensor according to an embodiment of the invention.
Figure 5B:
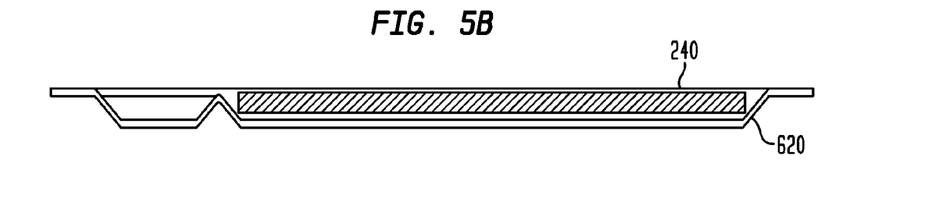

Turning now to FIGS. 5A and 5B, one embodiment of individually packaged test sensors 230 is illustrated. Packaged test sensor 230 includes a packaging base 620, a test sensor 150, a desiccant 235 and a cover, such as a foil cover 240. In the illustrated embodiment, packaging base 620 is at least partially divided into a first compartment 510 and a second compartment 520. In this embodiment, first compartment 510 is configured to accommodate a desiccant 235 and second compartment 520 is configured to accommodate test sensor 150. Burst foil cover 240 is configured to establish a seal with packaging base 620 so as to allow vapor contact between the desiccant 235 and the test sensor 150 while substantially isolating the desiccant 235 and the test sensor 150 from ambient humidity and from other sensors in the cartridge. Each test sensor 150 is kept dry by desiccant 235 located inside first compartment 510 disposed adjacent to second compartment 520, which holds test sensor 150. First and second compartments 510, 520 in conjunction with burst cover foil 240 help prevent any contamination of test sensor 150 due to desiccant 235 and other external contaminants. Such test sensors 150 and desiccants 235 are known in the art and therefore are not described in further detail for sake of brevity. For example, such a test sensor is described in U.S. Pat. No. 7,118,668, which is hereby incorporated by reference in its entirety. Non-limiting examples of the desiccants include those available under the trademarks Desimax®, Drikette® and NatraSorb® and silica gel from Multisorb Technologies, Buffalo, N.Y.

In one embodiment, packaging base 620 may be made from an aluminum foil/plastic laminate or other such suitable materials having favorable characteristics such as rigidity, weight, and imperviousness to humidity. Sensor 150 may have dimensions of 3 mm (width)×16 mm (length) and package base 620 may have dimensions of 7.2 mm (width)×24 mm (length). The dimensions of test sensor 150, desiccant 235 and package base 620 may be adjusted according to the requirements of a given application. Foil cover 240 may be alternatively be comprised of different materials known in the art that are easily removable. For example, in an embodiment, the foil cover 240 may be a plastic film that is metalized with a thin coating of metal to prevent moisture from entering the sealed package 620. Yet another embodiment may include a foil cover 240 comprised of other materials known in the art that are easily removable such as polyester or polypropylene.

Figure 6:
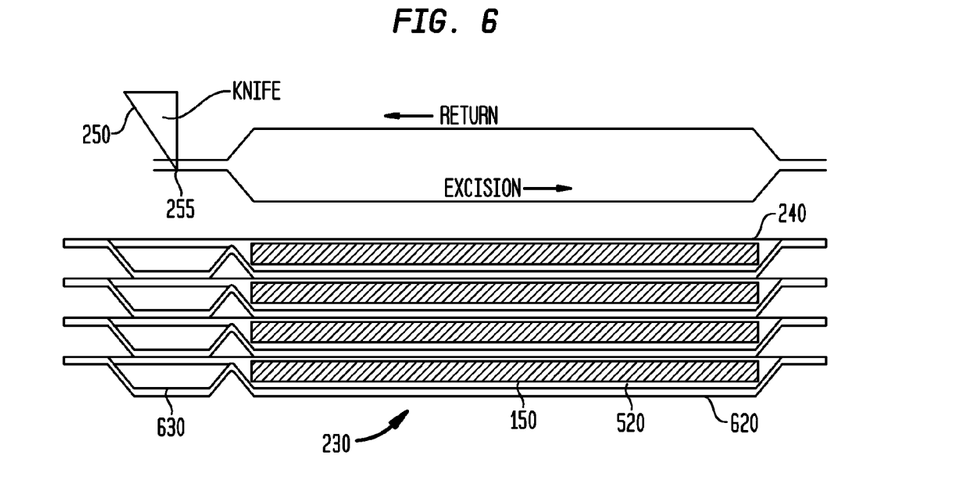
FIG. 6 is a schematic view of a knife mechanism for extracting a bio-sensor from a test sensor, according to an embodiment of the invention.

Referring now to FIG. 6, a knife mechanism 250 for extracting a test sensor 150 from the packaged test sensor 230 is illustrated schematically according to one embodiment. Upon user activation, the knife mechanism 250 travels to second compartment 520 and is lowered onto burst foil cover 240. Knife mechanism 250 pierces through burst foil cover 240 and an edge 255 of knife mechanism 250 engages an edge of the test sensor 150 proximal to the knife mechanism 250. Further movement of knife mechanism 250 causes test sensor 150 to move along with knife mechanism 250 and out of second compartment 520 of package 620. In an embodiment, the distal edge of the sensor 150 may be cut or configured to pierce through the foil cover 240, responsive to the urging by the knife mechanism 250. Once test sensor 150 is pushed out of second compartment 520 and is in position to receive a fluid sample, knife mechanism 250 is moved away relative to the stack of packaged test sensors 230 and returns to its original position. Moving knife mechanism 250 away from the stack of packaged test sensors 230 prevents accidental engagement of the edge 255 with a subsequent packaged test sensor 230. In an embodiment, knife mechanism 250 may travel back to its original position after dispensing test sensor 150 out of packaged test sensor 230. In an exemplary embodiment, the knife mechanism 250 may be spring-loaded such that after pushing out the test sensor 150, the knife mechanism 250 retracts away from the stack of the packaged sensors 230 and return to its initial position. In another embodiment, a user may manually push the knife mechanism 250 back to its initial position, for example, using a slider mechanism (not shown).

In another embodiment, knife mechanism 250 may travel back to its original position after the foremost packaged test sensor 230 from which test sensor 150 has been dispensed, is discarded from cartridge 200 (of FIG. 4) and test meter 100 (of FIG. 1). Movement of the knife mechanism 250 is discussed more fully herein.

Figure 7A:
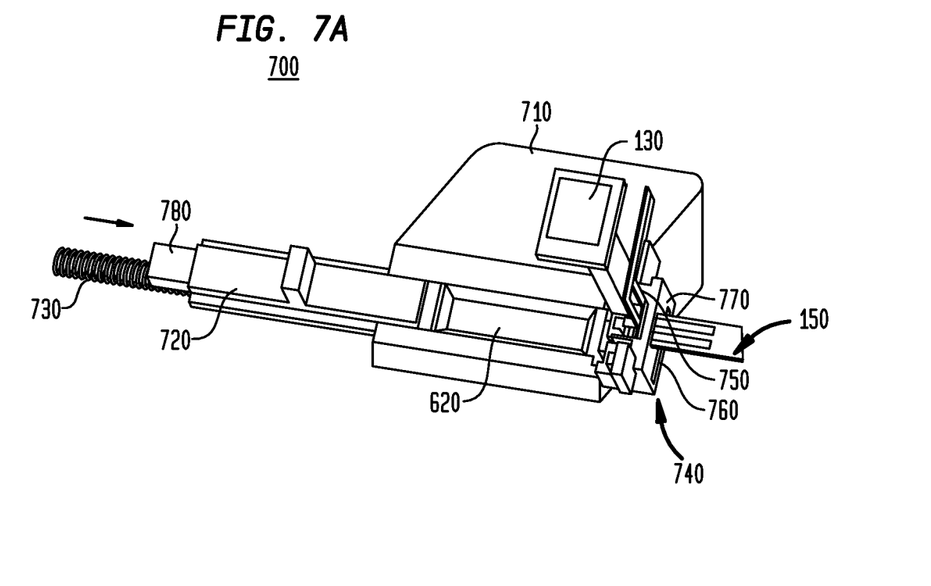
FIG. 7A is a partial exploded front view of the cartridge along with selected elements of the test meter of FIG. 3, according to an embodiment of the invention.
Figure 7B:
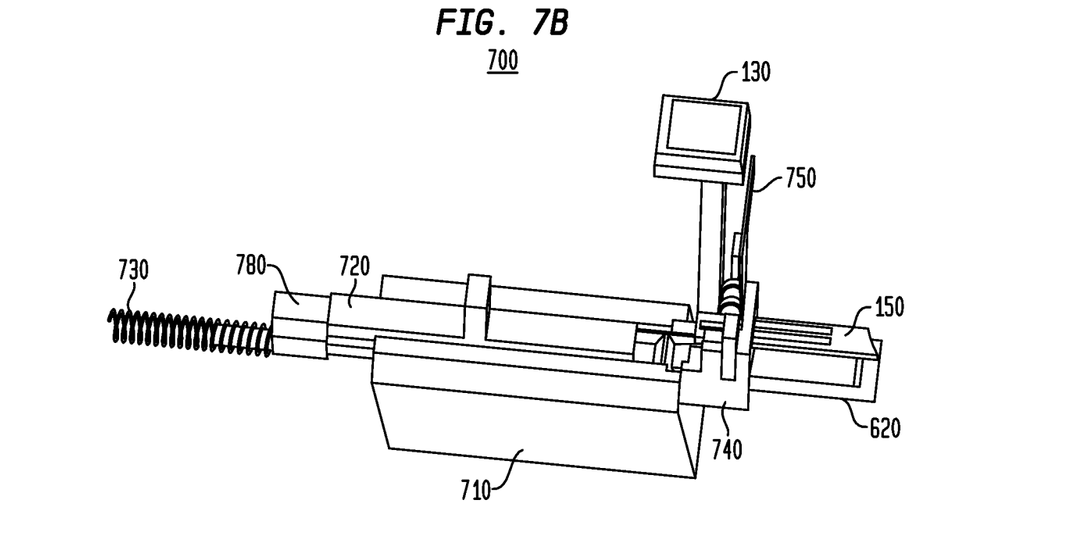
FIG. 7B is a partial exploded top view of the cartridge along with selected elements of the test meter of FIG. 3, according to an embodiment of the invention.

Now referring to FIGS. 7A and 7B, a cartridge 700 is partially illustrated with selected elements from test meter 100, according to one embodiment. Illustrated are a spring 730, a pusher 780, a blister eject slider 720, a contact platform 740, and a pair of contacts 750. As shown, a test sensor 150 is illustrated as being dispensed from package 620, extending through an opening or slot 770, and held in position by contact platform 740 so as to receive a fluid sample. Pair of contacts 750 engages test sensor 150 extending from test meter 100. Pair of contacts 750 includes terminals that electrically couple the electrodes to a meter (not shown) in test meter 100 for measuring the oxidation current produced at the electrodes by the reaction of an analyte in the fluid sample and the reagent.

The contact platform 740 is configured to hold test sensor 150 while test sensor is in position to receive a fluid sample, as well as to dispense a test sensor 150 and package 620 from test meter 100. Contact platform 740 includes the test sensor slot 770 and a package slot 760 through which test sensor 150 and package 620 may be discarded, respectively. Contact platform 740 is further configured to move relative to cartridge 710 when it receives test sensor 150 and package 620 therefrom. When knife mechanism 250 (FIG. 6) urges test sensor 150 out of package 620, contact platform 740 is aligned with the foremost packaged sensor 230 such that test sensor 150 enters test sensor slot 770 and extends out of test meter 100 through the slot 770 in test meter 100. (FIG. 3.) Pair of contacts 750 holds test sensor 150 in this position for receiving a fluid sample. When test sensor 150 is held in a position wherein one end is fixed and the other end extends from test meter 100, package 620 is urged against contact platform 740 by eject spring 730 and pusher 780. When empty package 620 needs to be ejected from test meter 100, contact platform 740 is moved up from the stack so as to align package slot 760 to align with package 620. Eject spring 730 and pusher 780 push package 620 out of test meter 100 through package slot 760, as illustrated in FIG. 7B. In this embodiment, a user can remove used test sensor 150 and empty package 620 from test meter 100 and discard the same. In another embodiment, one or more biasing mechanism may be provided to eject used test sensor 150 and empty package 620 from test meter 100.

The operation of test meter 100, according to an embodiment will now be described. A user loads a cartridge 210 of packaged test sensors 230 into test meter 100. The user slides slide driver 140 to the left or away from opening 170 in test meter 100, as shown in FIG. 3. The sliding of slide driver 140 causes the test meter 100 to turn on in an exemplary embodiment. When the slide driver 720 (FIG. 7A) is moved out of the way, it reveals opening 170 in the test meter housing that exposes the packaged sensor 230 at the top of the stack of packaged sensors in the cartridge 210. In an exemplary embodiment, the knife mechanism 250 (FIG. 6) may be integrated into or along with the slide driver 140 such that initial movement of the slide driver 140 pushes the topmost or foremost packaged sensor 230 to a predetermined position relative to the contact platform 740 and further movement of the slide driver 140 activates the knife mechanism 250 to push the test sensor 150 out of the package 620 as explained above.

The packaged test sensor 230 is pushed toward open end 205 of the housing 210 and into a dispensing position, for example, by a force applied to the bottom of the stack. The force may be a biasing force, such as by a spring (not shown) either in the cartridge or the meter. When the user slides slide driver 720 to the right toward the slot 170, as shown in FIG. 3, knife mechanism 250 follows the lower path (illustrated in FIG. 6) bursting through the burst cover foil 240 and presenting test sensor 150 for a test through the slot 170. Meter contacts (not shown) are now engaged with test sensor contacts 750. Blister package 620 is moved to the right until it contacts the contact platform 740. The user may then apply a fluid sample to test sensor 150 and an analyte, for example, glucose, is analyzed. The user then presses sensor release button 130 (FIG. 3) and the meter contacts (not shown) disengage from contacts 750 and test sensor 150 is released and at the same time slide drive 740 pushes blister package 620 out of test meter 100 for disposal and test meter 100 shuts off after a period of time.

Turning now to FIG. 8, another embodiment of the invention is illustrated schematically. Although the stack of packaged test sensors 230 is illustrated as a vertical stack with packaged test sensors 230 disposed horizontally, for simplicity and ease of understanding, packaged test sensors 230 may also be disposed with a tilt, for example, as previously discussed with regard to FIG. 4. A wall 810 of test meter 100 is also illustrated schematically with other elements of test meter 100 not shown for the sake of clarity. In an exemplary embodiment, contact platform 890 includes a rigid support structure 890, a foam layer 895 disposed thereupon and another support layer 897 disposed on the foam layer 895. Foam layer 895 is compressible to provide for proper alignment between the packaged test sensor 230 and test sensor 150 and the sensor slot 770 (of FIG. 7) and package slot 760 (of FIG. 7), respectively.

Figure 8A:
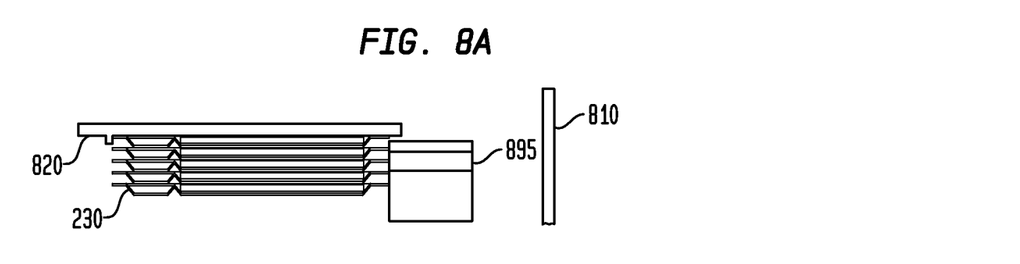
FIGS. 8A-8E illustrate schematically various stages of operation of a test meter using a stack of individually packaged test sensors, according to an embodiment of the invention.
Figure 8B:
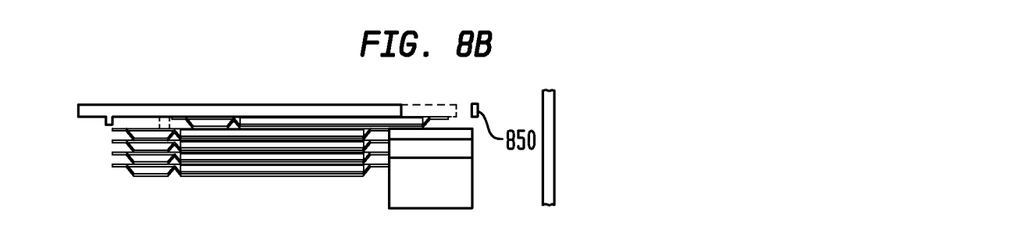
Figure 8C:
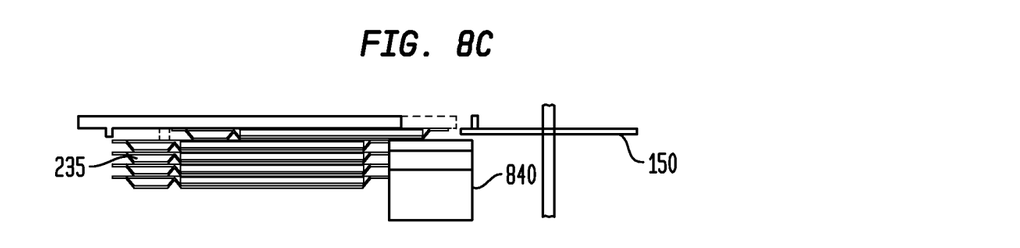
Figure 8D:
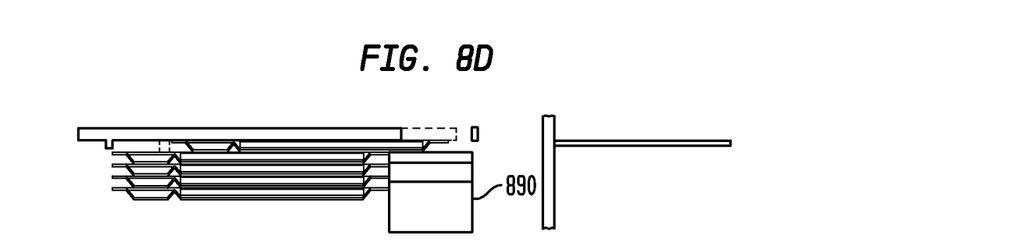
Figure 8E:
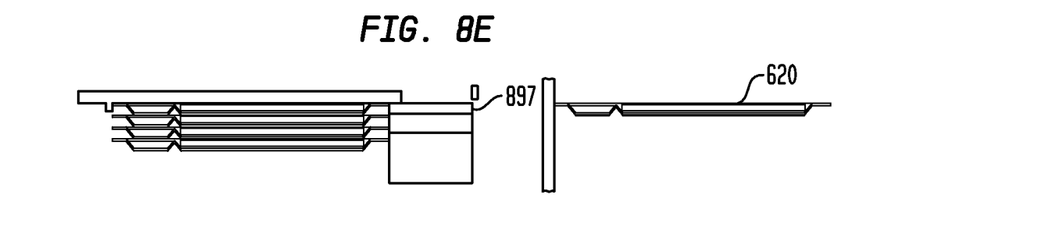
Figure 9A:
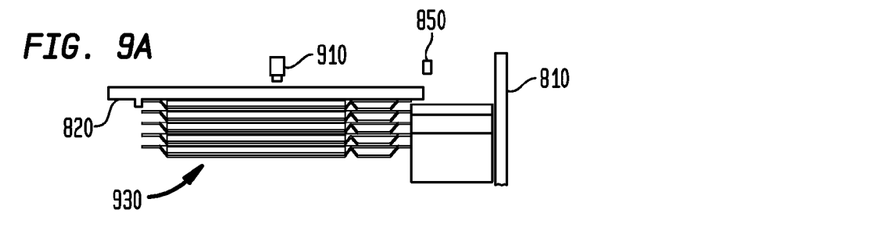
FIGS. 9A-9F illustrate schematically various stages of operation of a test meter using a stack of individually packaged test sensors, according to another embodiment of the invention.
Figure 9B:
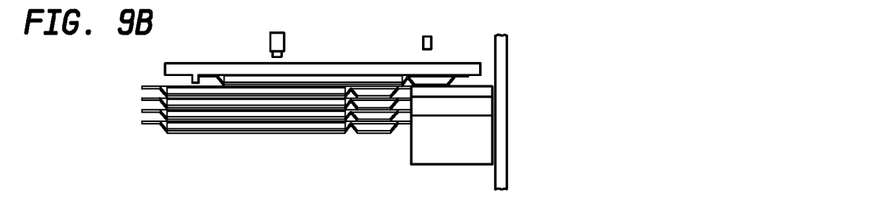
Figure 9C:
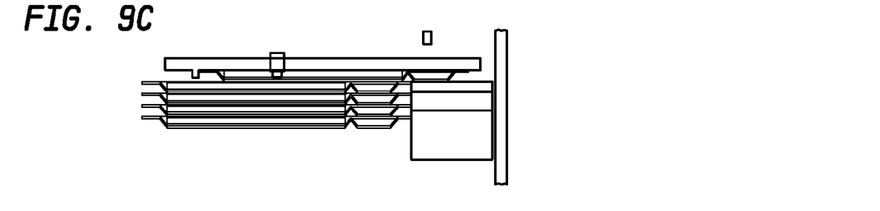
Figure 9D:
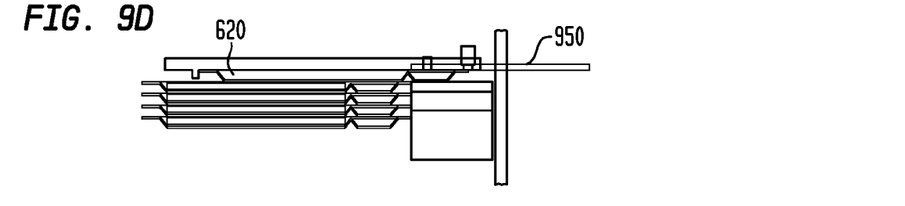
Figure 9E:
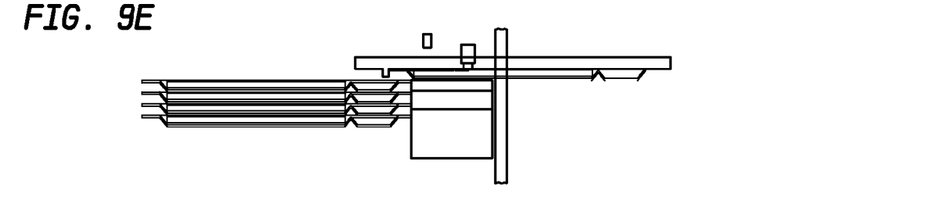
Figure 9F:
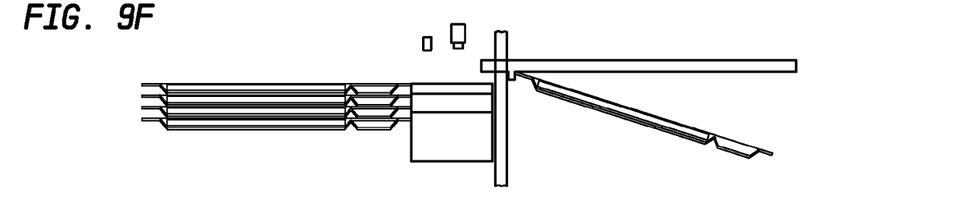
Figure 10A:
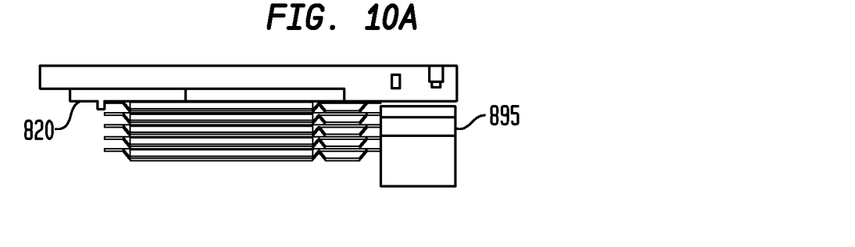
FIGS. 10A-10E illustrate schematically various stages of operation of a test meter using a stack of individually packaged test sensors, according to yet another embodiment of the invention.
Figure 10B:
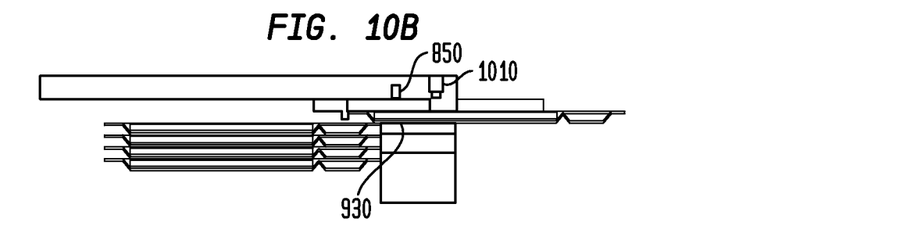
Figure 10C:
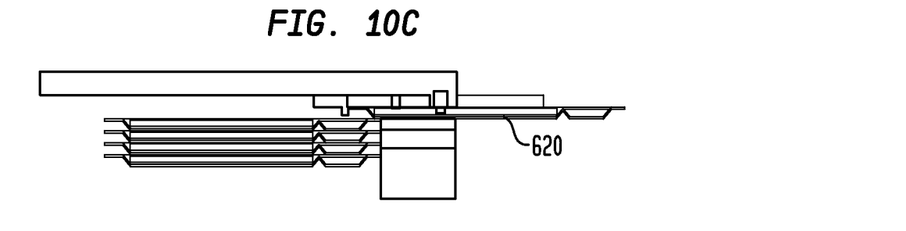
Figure 10D:
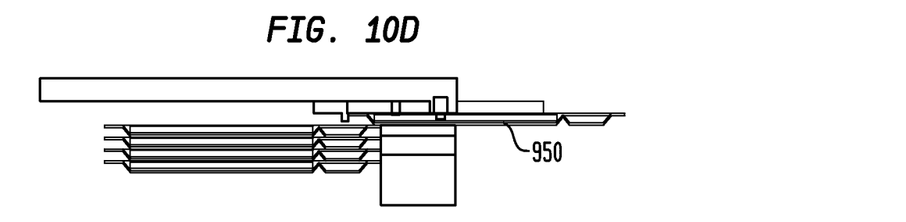
Figure 10E:
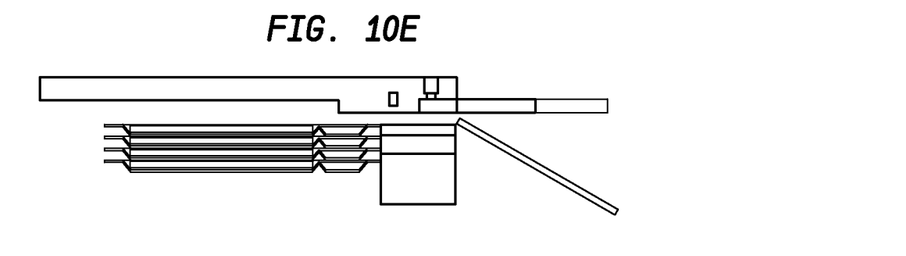

FIG. 8(a) illustrates the initial stage of operation of a test meter. Upon activation of the test meter by a user, a slider 820 urges the foremost packaged test sensor 230 toward meter wall 810, as illustrated in FIG. 8(b). FIG. 8(c) illustrates the subsequent stage, wherein a knife mechanism (for example, such as one illustrated in FIG. 6) pierces through burst foil cover 240 (of FIGS. 5A and 5B) and engages test sensor 150 to push test sensor 150 out of package 620. Test sensor 150 extends from meter wall 810 to receive, for example, a blood sample. Pair of contacts 850 engages test sensor 150 and couples with the electrodes to a meter (not shown) in test meter 100 for measuring the oxidation current produced at the electrodes by the reaction of glucose and the reagent. After the completion of the test, test sensor 150 may be discarded, as illustrated in FIG. 8(d). In FIG. 8(e), the empty package 620 may be urged out of meter 100 by slider 820 and subsequently slider 820 returns to its original position and engages the foremost packaged test sensor 230. In the illustrated embodiment, packaged test sensor 230 is disposed such that desiccant 235 is positioned on the end of strip 230 facing away from contact platform 840. An advantage of the illustrated embodiment is that the travel of test sensor 150 toward meter wall 810 is reduced as compared to that in an arrangement wherein desiccant 235 faces contact platform 840.

Turning to FIG. 9, yet another embodiment of the invention is illustrated schematically. The construction of a test meter according to the embodiment of FIG. 9 is generally similar to that illustrated in FIG. 8, except for the differences noted below. A test sensor 950 (FIG. 9C) of a packaged test sensor 930 is equipped with a slot (not shown), which may be, by way of non-limiting example, a circular slot. Instead of the knife mechanism 250 of FIG. 8, the test meter may include a test sensor drive pin 910 configured to establish a friction contact with the slot (not shown) in test sensor 950. Upon actuation by a user, test sensor drive pin 910 pierces through burst foil cover 240 and engages test sensor 950. Drive pin 910 then urges test sensor 950 to a test position, wherein test sensor 950 extends from meter wall 810 to receive, for example, a blood sample, as illustrated in FIG. 9(d). A reaction of analyte in the blood sample generates a response that can be read, for example, electrochemically, by optical absorbance, by reflectance or by fluorescence. The movement of the drive pin 910 engaged with test sensor 950 may be sufficient to pierce through the rest of burst cover foil 240 and extract test sensor 950 out of package 620. As shown in FIG. 9(e), after the completion of the test, while test sensor 950 is still in the read position, slider 820 urges empty package 620 such that test sensor 950 is disposed back in its initial position in the package 620. In the final stage, package 620 along with test sensor 950 is discarded from the meter, as illustrated in FIG. 9(f), either manually or automatically.

Referring now to FIG. 10, yet another embodiment of the invention is illustrated schematically. The construction of a test meter according to the embodiment of FIG. 10 is generally similar to that illustrated in FIG. 9, except for the differences noted below. FIG. 10(a) illustrates the initial stage, wherein the test meter is ready for use. Upon activation by a user, slider 820 urges packaged test sensor 930 to extend out from the meter (not shown), as shown in FIG. 10(b). As illustrated in FIG. 10(c), a test sensor retention pin 1010 pierces through burst foil cover 240 and engages test sensor 950. The user then pulls off package 620 and burst cover foil 240, to expose test sensor 950, as shown in FIG. 10(d). The test sensor 950 is now exposed and ready to receive, for example, a blood sample. According to an embodiment of the invention, package 620 and burst cover foil 240 may be sufficiently removed to expose test sensor 950 by the user, while still remaining associated (not shown) with test sensor 950 and/or the test meter. After the completion of the test, test sensor retention pin 1010 is activated to disengage from test sensor 950 and slider 820 automatically discards used test sensor 950 out of the test meter. An advantage of the illustrated embodiment is that no handling of a used test sensor 950 on the part of a user is necessary.

Having a plurality of packaged test sensors in a cartridge allows for a simple lever movement or a button press (such as button 130 of FIG. 1) to bring the test sensor into the testing position and eliminate user handling of bottles and individual sensors. Individually packaging each sensor also eliminates the need to unseal/seal sensor packaging each time a test is performed. Damage or a jamming of one individual sensor package does not damage or adversely affect the remaining packages of the cartridge, whereas a resealable cartridge seal failure or jam could lead to the loss of the remaining cartridge contents or of the meter itself. The cartridge itself can be simple and inexpensive because it has to simply mechanically contain the individually packaged test sensors without needing any seal or sensor lift mechanism or desiccant.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A device for testing an amount of an analyte in a fluid sample, the device comprising:
    a device housing having a front end, a rear end, a first opening positioned between the front end and the rear end, and a second opening positioned at the front end;
    a cartridge disposed in the device housing;
    a plurality of test strip packages in a stacked arrangement within the cartridge, each of the test strip packages comprising a packaging housing, a test sensor positioned within the packaging housing, and a cover sealing the test sensor within the packaging housing;
    a drive mechanism associated with the device housing and aligned with the second opening, the drive mechanism configured to engage one of the plurality of test strip packages and to move the one of the plurality of test strip packages relative to other test strip packages in the stacked arrangement;
    a knife mechanism associated with the drive mechanism, the knife mechanism configured to pierce the cover of the one of the plurality of test strip packages and to urge the test sensor out of the packaging housing and into the first opening,
    wherein the plurality of test strip packages is stacked at a non-perpendicular angle relative to a vertical wall of the cartridge.

2. The testing device of claim 1, wherein the first opening in the device housing is angled relative to the rear end of the device housing.

3. The testing device of claim 1, wherein the test strip packages are positioned at an angle relative to the rear end of the device housing.

4. The testing device of claim 3, wherein the angle of the test strip packages ranges from about 0 degrees to about 60 degrees.

5. The testing device of claim 1, wherein each of the plurality of test strip packages have a first end and a second end, each first end and each second end of each of the plurality of test stripe packages being aligned with one another.

6. The device of claim 1, wherein each of the plurality of test strip packages is biased toward the front end.

7. The testing device of claim 1, wherein each of the plurality of test strip packages have a first end and a second end, each first end and each second end of each of the plurality of test strip packages being collinear.

8. The testing device of claim 1, wherein the test strip packages further comprise a desiccant.

9. The testing device of claim 8, wherein the test strip packages comprise first and second compartments, the first compartment configured to receive the test sensor and the second compartment configured to receive the desiccant.

10. The testing device of claim 1,
    further comprising a third opening positioned between the front end and the rear end of the housing configured to receive one of the plurality of test strip packages therethrough after a test sensor has been removed from the packaging housing.

11. The testing device of claim 1, further comprising a device contact configured to engage a test sensor when the test sensor extends through the first opening to allow for electrical communication between the test sensor and the device housing.

12. The testing device of claim 1, wherein a height of the cartridge is smaller than a height of the plurality of test strip packages in the stacked arrangement.

13. A method for testing an analyte in a fluid sample comprising:

displacing, using a first mechanism, a test strip package from a stack of test strip packages in a cartridge in a test meter housing so that at least two opposed edges of the displaced test strip package are not aligned with corresponding edges of a remaining plurality of test strip packages in the stack, the stack of test strip packages stacked at a non-perpendicular angle relative to a vertical wall of the cartridge;

removing, using a second mechanism, a test sensor from within the test strip package and urging the test strip sensor through an opening of the test meter housing for receiving the fluid sample.

14. The method of claim 13, further comprising removing a remainder of the test strip package from the test meter housing.

15. The method of claim 13, further comprising biasing the remaining plurality of test strip packages towards the top of the stack of test strip packages.

16. The method of claim 13, further comprising cutting a seal on the test strip package prior to removing the test sensor.

17. The method of claim 13, wherein a desiccant is disposed in the test strip package.

18. The method of claim 13, wherein
the second mechanism comprises a knife mechanism.

19. The method of claim 13, wherein
the first mechanism comprises a slide mechanism.

* * * * *

UNITED STATES PATENT AND TRADEMARK OFFICE
CERTIFICATE OF CORRECTION

PATENT NO. : 8,940,540 B2  Page 1 of 1
APPLICATION NO. : 13/796093
DATED : January 27, 2015
INVENTOR(S) : Steven C. Charlton et al.

It is certified that error appears in the above-identified patent and that said Letters Patent is hereby corrected as shown below:

IN THE CLAIMS

In Column 10, Line 39, in Claim 5, delete "test stripe" and insert -- test strip --, therefor.

In Column 10, Line 40, in Claim 6, delete "The device" and insert -- The testing device --, therefor.

In Column 11, Line 10, in Claim 13, delete "test strip" and insert -- test --, therefor. (2nd occurrence)

Signed and Sealed this
Sixth Day of October, 2015

Michelle K. Lee
*Director of the United States Patent and Trademark Office*